(12) United States Patent
Ko et al.

(10) Patent No.: US 11,708,598 B2
(45) Date of Patent: Jul. 25, 2023

(54) COMPOSITION FOR POLYMERASE REACTION

(71) Applicant: NANOHELIX CO., LTD., Daejeon (KR)

(72) Inventors: Minsu Ko, Seoul (KR); Youngmi Lee, Daejeon (KR); Kayoung Lee, Daejeon (KR); Junsang Ko, Daejeon (KR)

(73) Assignee: NANOHELIX CO., LTD., Daejeon (KR)

( * ) Notice: Subject to any disclaimer, the term of this patent is extended or adjusted under 35 U.S.C. 154(b) by 702 days.

(21) Appl. No.: 16/484,192

(22) PCT Filed: Nov. 21, 2017

(86) PCT No.: PCT/KR2017/013229
§ 371 (c)(1),
(2) Date: Aug. 7, 2019

(87) PCT Pub. No.: WO2019/103164
PCT Pub. Date: May 31, 2019

(65) Prior Publication Data
US 2019/0360021 A1    Nov. 28, 2019

(51) Int. Cl.
*C12Q 1/6806* (2018.01)
*C12Q 1/6848* (2018.01)
*B01L 3/00* (2006.01)
*C12N 9/96* (2006.01)

(52) U.S. Cl.
CPC .......... *C12Q 1/6806* (2013.01); *B01L 3/5082* (2013.01); *C12N 9/96* (2013.01); *C12Q 1/6848* (2013.01); *B01L 2300/12* (2013.01); *B01L 2300/16* (2013.01)

(58) Field of Classification Search
CPC .... C12Q 1/6806; C12Q 1/6848; C12Q 1/686; C12Q 2531/113; C12N 9/96; B01L 2300/16
See application file for complete search history.

(56) References Cited

U.S. PATENT DOCUMENTS

| | | | | |
|---|---|---|---|---|
| 5,614,365 A * | 3/1997 | Tabor | ................. | C12Q 1/6869 435/488 |
| 6,117,634 A * | 9/2000 | Langmore | ............ | C12Q 1/6869 435/6.12 |
| 6,127,155 A | 10/2000 | Gelfand et al. | | |
| 6,242,235 B1 | 6/2001 | Shultz et al. | | |
| 8,822,670 B2 | 9/2014 | Kinoshita et al. | | |
| 2002/0102604 A1 * | 8/2002 | Milne Edwards | ..... | C07K 14/47 435/7.1 |
| 2004/0219546 A1 | 11/2004 | Sakaki et al. | | |
| 2005/0170375 A1 * | 8/2005 | Scherf | .................... | C12Q 1/68 435/91.2 |
| 2006/0068433 A1 * | 3/2006 | Godfrey | ............... | C12Q 1/6886 435/6.1 |
| 2009/0042190 A1 | 2/2009 | Kinoshita et al. | | |
| 2010/0173394 A1 * | 7/2010 | Colston, Jr. | ............. | B01L 7/525 422/68.1 |
| 2011/0020818 A1 * | 1/2011 | Sun | ........................ | B01L 3/508 435/6.12 |
| 2011/0118151 A1 * | 5/2011 | Eshoo | ..................... | C12P 19/34 435/287.2 |
| 2018/0163270 A1 * | 6/2018 | McDowell-Buchanan | ................. | C07K 16/12 |

FOREIGN PATENT DOCUMENTS

| EP | 1970440 | 9/2008 |
|---|---|---|
| KR | 10-1272447 | 6/2013 |
| WO | 2008/013885 | 1/2008 |

OTHER PUBLICATIONS

Ishihara et al. Advanced nanobiomedical application of the phosphorylcholine-polymer surface technology (PCST). 2006.. (Year: 2006).*
Tanaka et al. Analytical Sciences 2009; 25: 109-114. (Year: 2009).*
Nagai et al. Biochemistry and Molecular Biology International 1998; 44: 157-163. (Year: 1998).*
Life Science Product Information from NOF Corporation. Accessed from URL: <www.nof.co.jp/english/business/life/product05.html> on Apr. 6, 2022. (Year: None).*
Xu et al. Biomaterials 2009; 30: 4930-4938. (Year: 2009).*
Yoon et al. Mechanisms of Benzene-Induced Hematotoxicity and Leukemogenicity: cDNA Microarray Analyses Using Mouse Bone Marrow Tissue. Environmental Health Perspectives 2003; 111: 1411-1420 (Year: 2003).*
Brachat et al. A microarray-based, integrated approach to identify novel regulators of cancer drug response and apoptosis. Oncogene 2002; 21: 8361-8371 (Year: 2002).*

(Continued)

*Primary Examiner* — Angela M. Bertagna
(74) *Attorney, Agent, or Firm* — Hamre, Schumann, Mueller & Larson, P.C.

(57) ABSTRACT

Provided are a composition for a polymerase reaction, containing a nucleic acid polymerase and a 2-methacryloyloxyethyl phosphorylcholine (MPC)-containing zwitterionic copolymer detergent, a tube for a polymerase reaction, and a kit for a polymerase reaction. The stability of the composition for a polymerase reaction can be improved and the reliability of the results of polymerase reaction such as nucleic acid polymerization or amplification can be improved.

16 Claims, 4 Drawing Sheets

Specification includes a Sequence Listing.

(56) References Cited

OTHER PUBLICATIONS

Fixe, F. et al., "Functionalization of poly(methyl methacrylate) (PMMA) as a substrate for DNA microarrays", Nucleic Acids Research, 2004, vol. 32, No. 1, e9, pp. 1-8.
International Search Report and Written Opinion issued for PCT/KR2017/013229, dated Aug. 20, 2018, 10 pages, with English translation of International Search Report.

* cited by examiner

Amplifications of detergent-free PCR in the tubes coated with several detergents.

PC, positive control (PCR reaction with final 0.01% NP-40 and 0.01% TWEEN 20);
NC, negative control (PCR reaction without NP-40 and TWEEN 20);
NTC, No Template Control;
1, Coated with NP-40 and TWEEN 20; 2, Coated with Biolipidure 206; 3, Coated with Biolipidure 802

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: forward primer

<400> SEQUENCE: 1
tagattcttt ccggcagcac                                           20

<210> SEQ ID NO 2
<211> LENGTH: 20
<212> TYPE: DNA
<213> ORGANISM: Artificial Sequence
<220> FEATURE:
<223> OTHER INFORMATION: reverse primer

<400> SEQUENCE: 2
actccacatc ctcacgtatc                                           20
```

COMPOSITION FOR POLYMERASE REACTION

STATEMENT REGARDING SEQUENCE LISTING

This application contains a Sequence Listing that has been submitted electronically in ASCII format and is hereby incorporated by reference in its entirety. Said ASCII copy, created on Jul. 5, 2022, is named Sequence Listing US-NNH-P1901_ST25.txt and is 578 bytes in size.

TECHNICAL FIELD

The present invention relates to a composition for a polymerase reaction, and more specifically, to a composition for a polymerase reaction including a novel detergent which improves the stability of a polymerase, a tube for a polymerase reaction, and a kit for a polymerase reaction.

BACKGROUND ART

The polymerase chain reaction (PCR) is a primary method in molecular biology that amplifies, among whole genes, a specific gene fragment the nucleotide sequence of which is known, by using a DNA polymerase to inspect and isolate the gene. This polymerase chain reaction has been one of the essential techniques in research and inspection in biochemistry, molecular biology, medical and clinical pathology.

During the PCR, the thermostable DNA polymerase repeatedly cycles between the low and high temperatures. Although the DNA polymerase is highly thermostable, it tends to be inactive at high temperatures over time.

A method of enzyme stabilization is to use a surfactant or detergent that stabilizes the interaction between the enzyme and its liquid surroundings. For example, U.S. Pat. No. 6,127,155 discloses the feature in which a non-ionic polymeric detergent such as polyethoxylated sorbitan monolaurate (Tween 20) and ethoxylated alkylphenol 4-nonylphenyl-polyethylene glycol (Nonidet P-40) contained in a storage buffer stabilizes a Taq DNA polymerase. However, in some applications, it is known that a DNA polymerase stabilized with Tween 20 has a low amplification efficiency or amplifies non-specific products, and that a detergent such as Nonidet P-40 has toxicity.

With regard to detergents used for stabilization of nucleic acid polymerase, U.S. Pat. No. 6,242,235 discloses the use of a polyethoxylated surfactant, and International Patent Publication No. WO 2008/013885 discloses a reaction mixture for a polymerase chain reaction including a purified polymerase, an oligonucleotide probe, a detectable label, and a zwitterionic detergent or a non-detergent surfactant. European Patent Application Laid-open No. EP1970440 discloses stabilization of polymerases in an aqueous solution by means of an ionic detergent, particularly a zwitterionic detergent in the presence of inert proteins such as BSA.

However, in some application examples, it is problematic in that these detergents cause non-specific amplifications, are toxic, or have poor storage stability at room temperature. Thus, there is a need to develop a detergent for a polymerase reaction, which improves the stability of a nucleic acid polymerase, particularly a detergent which improves the stability of an enzyme while having no drawbacks of conventional detergents.

DISCLOSURE OF THE INVENTION

Technical Problem

The present invention is directed to meet above-described technical requirements. One objective of the present invention is to provide a composition for a polymerase reaction which improves the stability of a polymerase reaction composition and is capable of enhancing the reliability of polymerase reaction results, the composition including a novel detergent for a polymerase reaction, which has no drawbacks of conventional detergents and improves the stability of a nucleic acid polymerase.

Another objective of the present invention is to provide a tube for a polymerase reaction coated with the detergent according to the present invention.

Yet another objective of the present invention is to provide a kit for a polymerase chain reaction (PCR) including the composition for a polymerase reaction.

Technical Solution

One aspect of the present invention to accomplish above-described objectives relates to a composition for a polymerase reaction, including a nucleic acid polymerase and a 2-methacryloyloxyethyl phosphorylcholine (MPC)-containing zwitterionic copolymer detergent.

In the present invention, the MPC-containing zwitterionic copolymer may include a zwitterionic 2-methacryloyloxyethyl phosphorylcholine (MPC) unit, and an alkyl methacrylate-based monomer unit functionalized by a cationic, an anionic, or a hydrophobic functional group.

Another aspect of the present invention relates to a kit including a reagent or the like necessary to perform a polymerase chain reaction or to prepare such a mixture.

Yet another aspect of the present invention relates to a tube for use in a polymerase chain reaction, wherein the inner surface of the tube is coated with the nucleic acid polymerase and the 2-methacryloyloxyethyl phosphorylcholine (MPC)-containing zwitterionic copolymer detergent according to the present invention.

Advantageous Effects

A nucleic acid polymerase and A 2-methacryloyloxyethyl phosphorylcholine (MPC)-containing zwitterionic copolymer detergent used herein are non-toxic and reduce non-specific amplification, thereby providing an effect of increasing the stability in nucleic acid polymerization or a nucleic acid polymerase in an amplification reaction solution.

A composition for a polymerase reaction according to the present invention has improved stability, thereby advantageously being applicable to the fields of animal and human diagnostics and food analysis, and the increase in the stability of the composition for a polymerase reaction provides more flexibility in transportation and storage.

Furthermore, since a composition according to the present invention provided for a polymerase reaction by a nucleic acid polymerase and a 2-methacryloyloxyethyl phosphorylcholine (MPC)-containing zwitterionic copolymer detergent can be stably stored, the polymerase reaction can be stabilized, thereby improving reliability of polymerase reaction results.

BEST MODE FOR CARRYING OUT THE INVENTION

Figure 1:
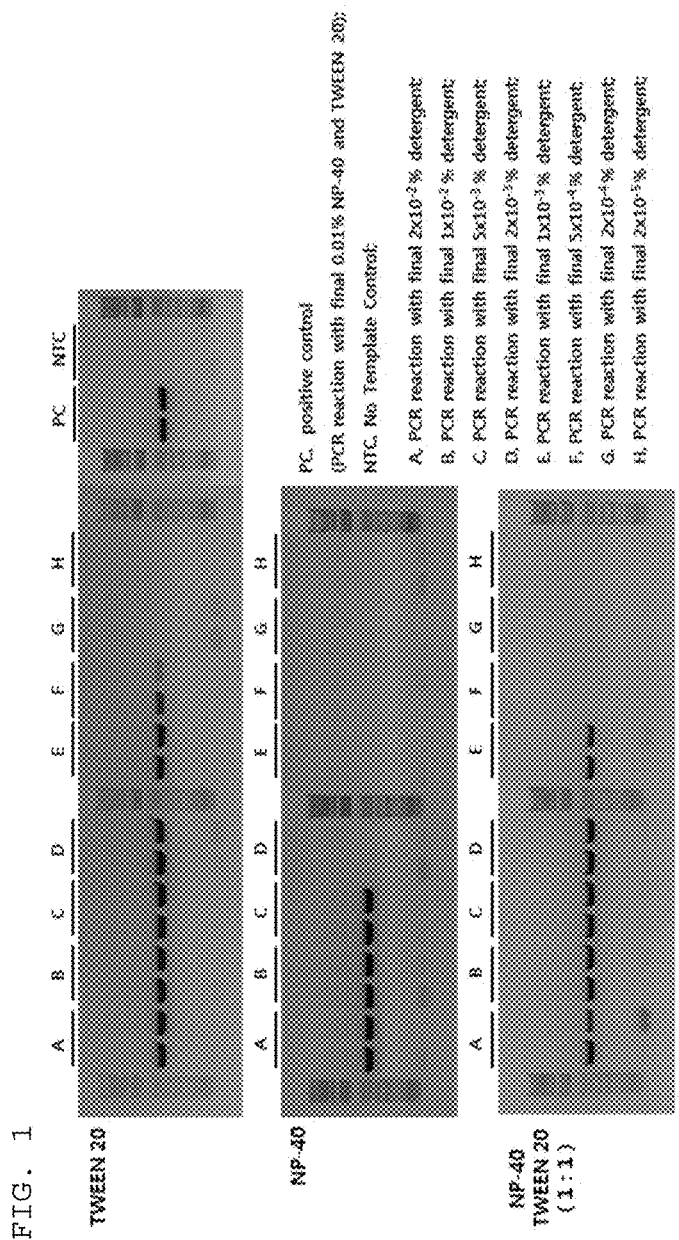
FIG. 1 shows PCR results when a conventional detergent (Tween 20 and Nonidet P-40) is used.

Hereinafter, the present invention will be described in more detail with reference to the drawings.

In order to more clearly and concisely describe the gist of the present invention, terms used herein are defined as follows. However, it will be understood that the meaning of these terms should be understood as non-limited examples.

The term "nucleic acid polymerase" in the present invention means an enzyme that extends oligonucleotides along a DNA or RNA template. In the present invention, the nucleic acid polymerase may be an RNA-dependent RNA-polymerase, an RNA-dependent DNA-polymerase, a DNA-dependent DNA-polymerase, and a DNA-dependent RNA-polymerase.

As used herein, the term "detergent" refers to an agent that, when added to a liquid for polymerase reaction, reduces the surface tension of a liquid as compared to the same liquid not containing a detergent. Such a detergent may store a composition for a polymerase reaction in a stable state, and thus exhibits effects of being capable of reducing deterioration of the composition for a polymerase reaction and stabilizing the polymerase reaction.

Nucleic acid "amplification" means for replicating a nucleic acid sequence from one into a number of additional copies in a manner catalyzed by an enzyme.

As used herein, the term "dNTP" refers to deoxynucleoside triphosphate. Purine bases (Pu) include adenine (A), guanine (G), and derivatives and analogs thereof. Pyrimidine base (Py) includes cytosine (C), thiamine (T), uracil (U), and derivatives and analogs thereof. Examples of such derivatives or analogs include those modified using fluorescent or chromogenic reporter groups, those biotinylated, those amine-modified, those radioactively labeled, and those alkylated, etc., and also include phosphorothioate, phosphite, ring atom-modified derivative, and the like.

As used herein, the term "sequence" refers to an oligonucleotide or a nucleotide sequence of a nucleic acid.

Throughout this specification, whenever an oligonucleotide/nucleic acid is represented by a series of letters, the nucleotides are present in the 5' to 3' order from left to right.

As used herein, the term "primer" or "primer sequence" refers to a short linear oligonucleotide that hybridizes to a target nucleic acid sequence to prime a nucleic acid synthesis reaction.

One aspect of the present invention relates to a composition for a polymerase reaction including a nucleic acid polymerase and a 2-methacryloyloxyethyl phosphorylcholine (MPC)-containing zwitterionic copolymer detergent.

The 2-methacryloyloxyethyl phosphorylcholine (MPC)-containing zwitterionic copolymer detergent contained in the composition according to the present invention may reduce the inactivation of a polymerase during the thermal cycling process of the polymerase reaction, and improve storage stability. This is presumably due to the effect of preventing each polymerase reaction composition from adhering to the surface of a storage container, the effect of preventing the aggregation of the reaction compositions, and the effect of preventing decomposition, by means of the 2-methacryloyloxyethyl phosphorylcholine (MPC)-containing zwitterionic copolymer detergent. Thus, the detergent, according to the present invention, can effectively replace conventional detergents having various drawbacks such as NP-40 or Tween 20.

The 2-methacryloyloxyethyl phosphorylcholine (MPC)-containing zwitterionic copolymer may include 2-methacryloyloxyethyl phosphorylcholine (MPC) unit, and an alkyl methacrylate-based monomer unit functionalized by a cationic, an anionic, or a hydrophobic functional group.

The 2-methacryloyloxyethyl phosphorylcholine (MPC) unit may be represented by formula 1 below.

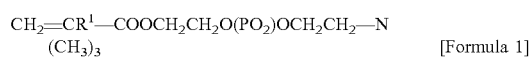

[Formula 1]

where, $R^1$ represents a hydrogen atom or a lower alkyl group having 1 to 4 carbon atoms.

Examples of the 2-methacryloyloxyethyl phosphorylcholine (MPC) unit may include 2-(acryloyloxy)ethyl-2-(trimethylammonium)ethyl phosphate and 2-(methyl acryloyloxy)ethyl-2-(trimethylammonium) ethyl phosphate.

Non-limiting examples of the alkyl methacrylate-based monomer unit may include methyl methacrylate, ethyl methacrylate, n-butyl methacrylate, methyl methacrylate, ethyl methacrylate, butyl methacrylate, pentyl methacrylate, hexyl methacrylate, heptyl methacrylate, octyl methacrylate, tridecyl methacrylate, 2-hydroxyethyl methacrylate, or the like.

In a specific embodiment, the zwitterionic copolymer includes a zwitterionic MPC unit and an alkyl methacrylate-based monomer unit functionalized by a hydrophobic functional group. The hydrophobic functional group includes a linear or branched $C_{4-30}$ alkyl group, a linear or branched $C_{4-30}$ cycloalkyl group, a $C_{4-30}$ hydrocarbon chain containing at least one double bond, a $C_{4-30}$ hydrocarbon chain containing at least one triple bond, or a $C_{4-30}$ hydrocarbon chain containing at least one aromatic ring.

Examples of the 2-methacryloyloxyethyl phosphorylcholine (MPC)-containing zwitterionic copolymer according to the present invention include Lipidure® Biolipidures, and specifically Biolipidure 206, Biolipidure 802, Biolipidure 1201 and Biolipidure 1301, commercially available from the NOF Corporation, but are not necessarily limited thereto.

The 2-methacryloyloxyethyl phosphorylcholine (MPC)-containing zwitterionic copolymer detergent according to the present invention has a Hydrophile-Lipophilic Balance (HLB) of 6 to 12, and preferably 8 to 12. For example, Biolipidure 206 has an HLB of 9.6, and Biolipidure 802 has an HLB of 10.9.

The 2-methacryloyloxyethyl phosphorylcholine (MPC)-containing zwitterionic copolymer may be prepared by mixing a 2-methacryloyloxyethyl phosphorylcholine (MPC) unit and an alkyl methacrylate-based monomer unit functionalized by a cationic, an anionic, or a hydrophobic functional group, and then copolymerizing the resultant mixture through radical polymerization, for example, through well-known methods such as bulk polymerization, suspension polymerization, emulsion polymerization, solution polymerization, inside a reactor in which an inert gas atmosphere is maintained by substituting nitrogen, carbon dioxide, helium or the like, in the presence of a polymerization initiator.

A solvent used for the solution polymerization may be appropriately selected, and alcohols such as methanol, ethanol and isopropanol, ethers such as diethyl ether, and organic solvents such as chloroform, may be used alone or in combination.

A radical polymerization initiator for the radical polymerization reaction may employ any one generally used. For example, the radical polymerization initiator may use azo-based polymerization initiators such as azoisobutylonitrile (AIBN) and azobisvaleronitrile; or lipophilic organic peroxides such as lauroyl peroxide, benzoyl peroxide, t-butyl peroxyneodecanoate, and t-butyl peroxy pivalate.

The molecular weight of the copolymer is a number average molecular weight of 1,000-2,000,000, and preferably 2,000-1,000,000. When the number average molecular weight is less than 1,000, it is difficult to stabilize the composition for a polymerase reaction; however, when the number average molecular weight is more than 1,000,000, the viscosity of the polymer may become too high to result in a difficulty in handling.

The composition for a polymerase reaction according to the present invention may further include at least one dNTP, and at least one nucleic acid amplification primer (for example, a PCR primer). In some specific examples, the polymerase is thermostable. Examples of such a polymerase may employ Taq polymerase, Tth polymerase, Tli or VENT polymerase, Pfu or DEEPVENT polymerase, Pwo polymerase, Bst polymerase, Sac polymerase, Tac polymerase, Tfl/Tub polymerase, Tru polymerase, DYNAZYME polymerase, Tne polymerase, Tma polymerase, Tsp polymerase, Mth polymerase, KOD DNA polymerase, or the like.

In this composition, the mixing ratio of the 2-methacryloyloxyethyl phosphorylcholine (MPC)-containing zwitterionic copolymer detergent is 0.001% w/v to 5.0% w/v, preferably 0.01% w/v or more, more preferably 0.5% w/v or more, and most preferably 0.5% w/v to 3.0% w/v, with respect to a reaction solution. When the mixing ratio is less than 0.001% w/v, the stabilizing action may be insufficient; and when the mixing ratio is more than 5.0% w/v, it is difficult to expect more additional synergistic effect even when more mixed.

In addition to the 2-methacryloyloxyethyl phosphorylcholine (MPC)-containing zwitterionic copolymer detergent, and the nucleic acid polymerase, the composition according to the present invention may further include a buffer, a monovalent salt, a divalent salt, a reducing agent, a chelating agent, and a mixture of dNTP.

A suitable buffer includes those that are well known in the art for use in the thermal cycling process. Depending on the specific application, the buffer may be a storage buffer or a reaction buffer. Independent of the specific application, the buffer maintains the pH of the composition at about 4.0 to about 9.5, preferably about 6.0 to about 9.0, and more typically about 7.5 to about 9.0. Representative examples of the suitable buffer include MOPS, HEPES, TAPS, Bicine, Tricine, TES, PIPES, MES, or Tris buffer. The storage buffer may further include a preservative solution such as glycerol, polyethylene glycol and/or BSA.

Furthermore, the composition for a polymerase reaction according to the present invention may also include a monovalent salt or a divalent salt. The suitable monovalent salt may include sodium chloride, potassium chloride, potassium acetate or lithium chloride, and representative examples of the suitable bivalent salt may include calcium chloride, manganese chloride, magnesium acetate or magnesium chloride, but are not limited thereto.

The composition, according to the present invention, may further include a reducing agent. The suitable reducing agent includes dithiothreitol, tris(2-carboxyethyl) phosphine hydrochloride, β-mercaptoethanol, sodium borohydride, oxalic acid, or lithium aluminum hydride. In a further embodiment, the composition for a polymerase reaction according to the present invention may include a chelating agent, and examples of the suitable chelating agent include EDTA or EGTA.

The composition for a polymerase reaction according to the present invention may be used for amplification of nucleic acids, in particular, for application to molecular biology such as, PCR, quantitative real-time PCR (qPCR), melting curve analysis, high-resolution melting analysis, sequencing, quantitative fluorescent PCR, multiplex PCR, digital PCR (dPCR), whole genome amplification (WGA), reverse transcription PCR, or isothermal polymerization reaction, but are not necessarily limited thereto.

Another aspect of the present invention relates to a tube for a polymerase reaction, which is produced by coating the inner surface of the tube with a 2-methacryloyloxyethyl phosphorylcholine (MPC)-containing zwitterionic copolymer detergent. The tube for a polymerase reaction tube coated with the detergent according to the present invention may cause PCR amplification reaction due to the detergent present on the inner surface of the tube even when a detergent is not contained in a PCR reaction solution.

In the present invention, a method for coating the tube with the detergent according to the present invention may employ any method known in the art without particular limitation. For example, a coated tube for a polymerase reaction may be obtained by preparing a coating solution through dilution of a detergent with sterilized water, putting the coating solution into a tube for a polymerase reaction, causing a reaction for a predetermined time (for example, about 30 minutes) at a room temperature, and then washing the tube with sterilized distilled water twice or more to remove the detergent remaining after the reaction.

Another aspect of the present invention relates to a kit including a composition for a polymerase reaction including the above-described 2-methacryloyloxyethyl phosphorylcholine (MPC)-containing zwitterionic copolymer detergent.

The PCR kit according to the present invention refers to a set in which a composition for a polymerase reaction including a detergent is packaged. The kit may further include a reducing agent, a buffer, a mixture of dNTP, an instruction for use of the composition, and other components required for a thermal cycling reaction to amplify a nucleic acid. The kit may also include a sample containing a predefined target nucleic acid which is used in a control group reaction. The kit may also optionally include a stock solution, buffer, enzyme, detectable label or reagent, required for detection, tube, membrane, etc., which may be used to complete the amplification reaction.

Hereinafter, the present invention will be described in more detail with reference to examples. These examples are only for illustrating, and the present invention is not limited to the examples below.

EXAMPLES

Comparative Example 1: Determination of the Effect Concentrations of Detergents, Nonidet™ P-40(NP-40) and Tween 20

To check available concentration ranges for conventional detergents, NP-40 and Tween 20, which are commonly used for polymerase reaction, the detergents were tested alone or in a 1:1 mixture form. Nonidet™ P40 substitute (available from SIGMA-ALDRICH) and Tween 20 (available from SIGMA-ALDRICH) were used as detergent products.

PCR analysis was performed such that the 850 bp fragment of human polD2 gene was amplified using a forward primer (5'-TAGATTCTTTCCGGCAGCAC-3') (SEQ ID NO:1) and a reverse primer (5'-ACTCCACATCCT-CACGTATC-3') (SEQ ID NO:2).

Reaction was performed with following cycling parameters, that is, reaction for 1 cycle at 95° C. for 15 minutes, then reaction for 35 cycles at 95° C. for 30 seconds, at 58° C. for 20 seconds, and at 72° C. for 40 seconds for 35 cycles, followed by reaction at 72° C. for 10 minutes. Aliquots of each reaction were analyzed by agarose gel electrophoresis.

Referring to FIG. 1, the effective concentrations of Tween 20, NP-40, and a mixture (in which Tween 20 and NP-40 were mixed at a ratio of 1:1) suitable for PCR amplification were $5 \times 10^{-4}\%$ v/v, $5 \times 10^{-3}\%$ v/v, $1 \times 10^{-3}\%$ v/v or more, respectively, in the reaction solution.

Experimental Example 1: Test of Effects of Detergent in PCR Reaction

A test was performed to check whether a 2-methacryloyloxyethyl phosphorylcholine (MPC)-containing zwitterionic copolymer (Examples 1 to 4), an MPC-containing anionic copolymer (Comparative Example 1), and an MPC-containing cationic copolymer (Comparative Example 2) had an ability to allow Taq DNA polymerase activity to be exhibited in PCR reaction. PCR was performed without using a detergent, as a negative control group (NC), and a mixture of Tween 20 and NP-40 was used as a detergent, as a positive control group (PC).

PCR analysis was performed such that the 850 bp fragment of the human polD2 gene was amplified using a forward primer (5'-TAGATTCTTTCCGGCAGCAC-3') (SEQ ID NO:1) and a reverse primer (5'-ACTCCA-CATCCTCACGTATC-3') (SEQ ID NO:2).

Reaction was performed with the following cycling parameters, that is, reaction for 1 cycle at 95° C. for 15 minutes, then reaction for 35 cycles at 95° C. for 30 seconds, at 58° C. for 20 seconds, and at 72° C. for 40 seconds, followed by reaction at 72° C. for 10 minutes. For each detergent tested, PCR was performed in a concentration range of 0.01% w/v to 1% w/v in the reaction solution, and a positive control group (PC) including 0.01% v/v of Tween 20 and 0.01% v/v of NP-40 (total 0.02% v/v), a negative control group (NC) in the absence of a detergent, and an NTC in the absence of a template, were included. Aliquots of each reaction were analyzed by agarose gel electrophoresis.

The composition for a polymerase chain reaction was prepared in a state in which a detergent is not contained by dialyzing a purified Taq polymerase using a Taq storage buffer (20 mM Tris at pH 9.0, 0.1 mM EDTA-NaOH at pH 8.0, 100 mM of KCl, 1 mM of PMSF, 1 mM of DTT), various 2-methacryloyloxyethyl phosphorylcholine (MPC)-containing copolymer detergents were added thereto at a mixing ratio ranging from 0.01 to 1.0% w/v, and then a polymerase reaction efficacy test was performed.

Figure 2:
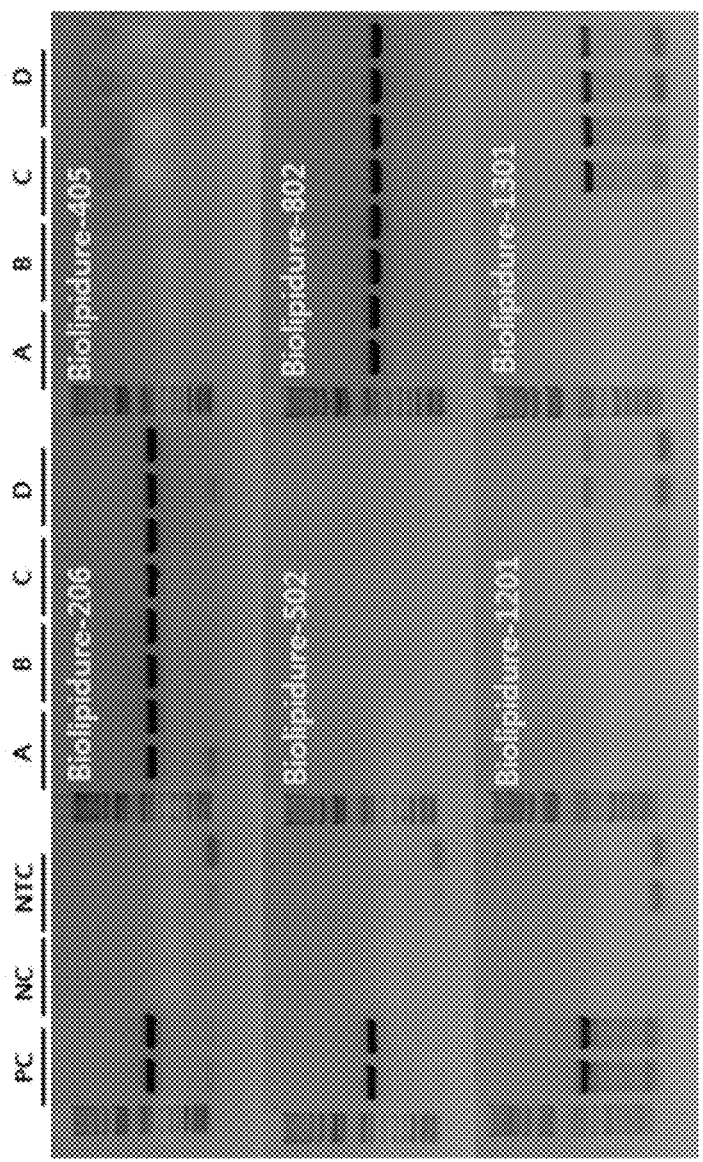
FIG. 2 shows PCR results when a novel detergent according to the present invention is used.

As shown in FIG. 2, Example 1 (Biolipidure 206), Example 2 (Biolipidure 802), Example 3 (Biolipidure 1201), and Example 4 (Biolipidure 1201) using 2-methacryloyloxyethyl phosphorylcholine (MPC)-containing zwitterionic copolymer detergents, were confirmed to promote PCR reaction. In contrast, the composition of Comparative Example 1 (Biolipidure 405) using an MPC-containing anionic copolymer, and Comparative Example 2 (Biolipi- dure 502) using an MPC-containing cationic copolymer exhibited no or extremely insignificant promotion of PCR reaction. As can be seen from the above results, it can be found that the 2-methacryloyloxyethyl phosphorylcholine (MPC)-containing zwitterionic copolymer detergent included in the composition for a polymerase reaction according to the present invention, can sufficiently replace conventional detergents used in PCR reaction.

Experimental Example 2: Determination of Effective Concentration of Novel Detergent to Promote PCR Reaction Four kinds of detergents, which were found to promote PCR reaction in Experimental Example 1, were applied to the PCR reaction solution having no detergents, at a concentration of up to 3% w/v in order to determine an effective concentration. The PCR promotion ability of a Taq polymerase-containing composition was assessed using PCR analysis which is similar to those described in Experimental Example 1. The primers and reaction conditions same as those in Experimental Example 1 were used.

Figure 3:
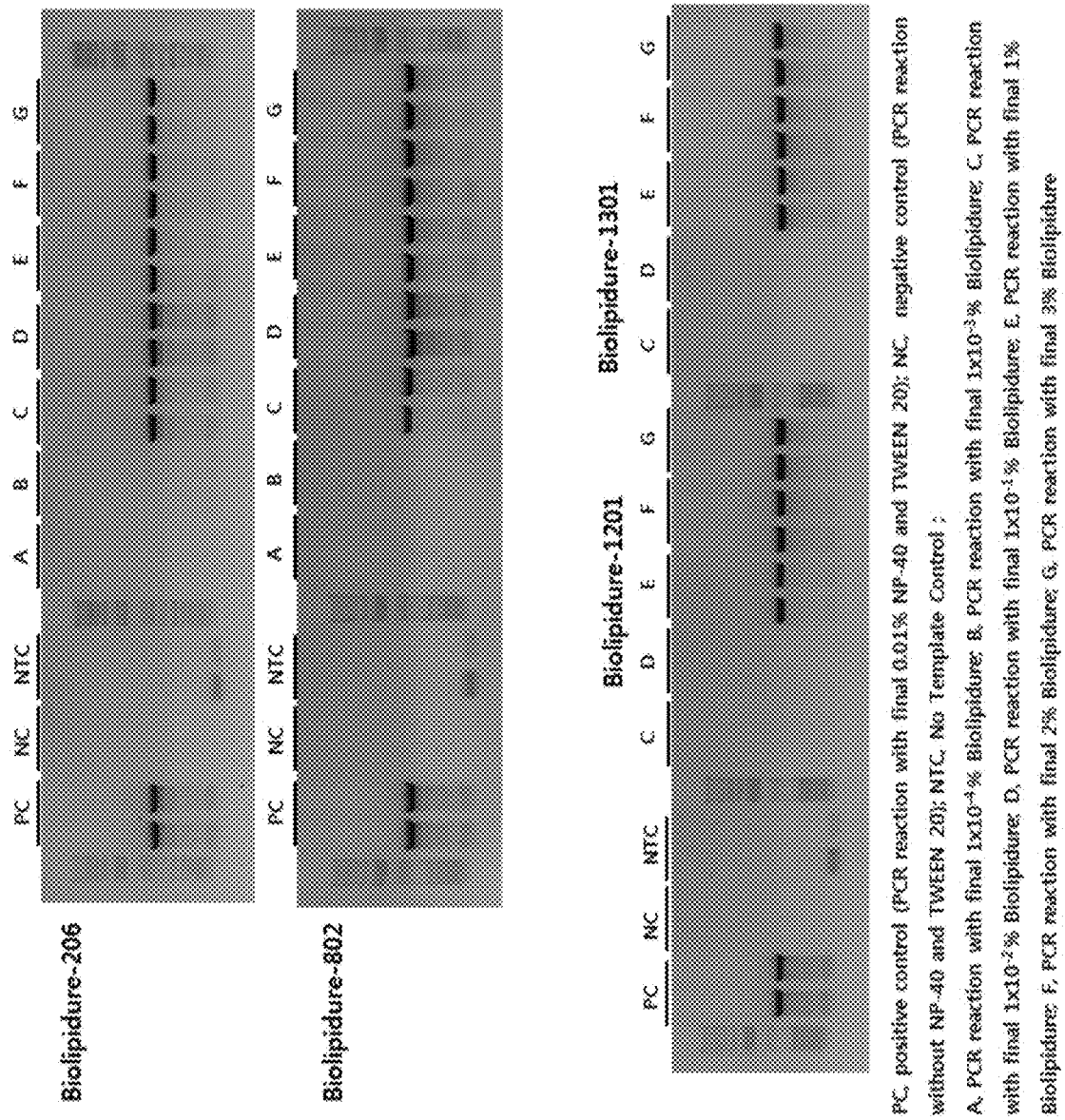
FIG. 3 shows PCR results when the concentration of the detergent according to the present invention is variously changed.

Referring to the results shown in FIG. 3, the composition of Example 1 (Biolipidure 206) showed PCR amplifications at 0.001% w/v or more, and exhibited an efficient amplification at 0.01% w/v or more. The composition of Example 2 (including Biolipidure 802) was effective at 0.01% w/v or more, and the compositions of Example 3 (Biolipidure 1201) and Example 4 (Biolipidure 1301) were effective at 0.5% w/v or more.

Experimental Example 3: Determination of PCR Tube Coating Effect of Novel Detergent The PCR tube coating was performed using the 2-methacryloyloxyethyl phosphorylcholine (MPC)-containing zwitterionic copolymer detergent according to the present invention. The test was carried out to check whether PCR amplification reaction occurs in a PCR reaction solution even in the absence of a detergent when the adsorption of DNA polymerase to plastic (PP/PE) tubes is prevented by tube coating.

1% w/v solutions of detergent of Tween 20/NP-40, Biolipidure 206, and Biolipidure 802 were prepared, respectively, and 100 µl of each solution was added to a 0.2 ml PCR tube. Detergent solutions were then left standing at room temperature for 1 hour and removed. The solution remaining in the tube was washed with sterilized water three times in a stepwise manner to be completely removed, and tubes coated with these detergents were prepared. The PCR reaction solution with no detergent added thereto was injected into the tube, and a PCR reaction was performed to confirm the amplification results. The results were assessed using PCR analysis, which is similar to those described in Experimental Example 1. The primers and reaction conditions same as those in Experimental Example 1 were used.

Figure 4:
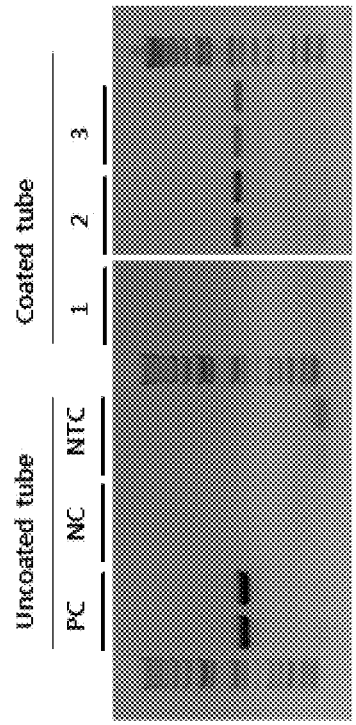
FIG. 4 shows PCR results when a PCR tube coated with the detergent according to the present invention is used.

Referring to FIG. 4, it can be seen that the PCR amplification was not observed in tubes which had not been subjected to coating, and tubes coated with Tween 20/NP-40, but the PCR amplification occurred in the tubes treated with Biolipidure 206 or Biolipidure 802.

The invention claimed is:

1. A composition for a polymerase reaction comprising:
a nucleic acid polymerase and a 2-methacryloyloxyethyl phosphorylcholine (MPC)-containing zwitterionic copolymer detergent,
wherein the composition comprises a reaction solution, the nucleic acid polymerase and the MPC-containing zwitterionic copolymer detergent are present in the reaction solution, and
the reaction solution is free of other detergent.

2. The composition of claim 1, wherein the MPC-containing zwitterionic copolymer detergent is a copolymer of a zwitterionic MPC unit and an alkyl methacrylate-based monomer unit functionalized by a cationic, an anionic, or a hydrophobic functional group.

3. The composition of claim 1, wherein the MPC-containing zwitterionic copolymer detergent has a weight-average molecular weight of 1,000-2,000,000.

4. The composition of claim 1, wherein the nucleic acid polymerase is an RNA-dependent RNA polymerase or an RNA-dependent DNA polymerase.

5. The composition of claim 1, wherein the nucleic acid polymerase is a DNA polymerase selected from the group consisting of Taq polymerase, Tth polymerase, Tli polymerase, Pfu polymerase, Pwo polymerase, Bst polymerase, Sac polymerase, Tac polymerase, Tfl/Tub polymerase, Tru polymerase, Tne polymerase, Tma polymerase, Tsp polymerase, Mth polymerase, and KOD DNA polymerase.

6. The composition of claim 1, wherein the MPC-containing zwitterionic copolymer detergent is contained in the reaction solution for a polymerase reaction at a concentration of 0.001% w/v to 5.0% w/v.

7. The composition of claim 1, further comprising a mixture of dNTPs selected from the group consisting of dATP, dCTP, dGTP, and dTTP.

8. The composition of claim 1, further comprising a reducing agent.

9. The composition of claim 1, further comprising a buffer to maintain the pH of the composition at 4.5 to 9.5.

10. The composition of claim 9, wherein the buffer is selected from the group consisting of MOPS, HEPES, TAPS, Bicine, Tricine, TES, PIPES, MES, and Tris.

11. The composition of claim 1, wherein the polymerase reaction is a PCR, a quantitative real-time PCR (qPCR), a sequencing reaction, a quantitative fluorescent PCR, a real-time PCR, a multiplex PCR, or a digital PCR (dPCR).

12. The composition of claim 1, wherein the polymerase reaction is a whole genome amplification (WGA).

13. The composition of claim 1, wherein the polymerase reaction is a reverse transcription PCR or an isothermal polymerization reaction.

14. The composition of claim 1, wherein the nucleic acid polymerase is a DNA-dependent DNA polymerase or an DNA-dependent RNA polymerase.

15. A PCR kit comprising the composition for a polymerase reaction of claim 1.

16. A reaction solution for a polymerase reaction comprising:
a nucleic acid polymerase and a 2-methacryloyloxyethyl phosphorylcholine (MPC)-containing zwitterionic copolymer detergent,
wherein the reaction solution is free of detergent other than the MPC-containing zwitterionic copolymer detergent.

* * * * *